United States Patent [19]

Balkányi et al.

[11] Patent Number: 4,619,936
[45] Date of Patent: Oct. 28, 1986

[54] PHARMACEUTICAL COMPOSITIONS HAVING APPETITE REDUCING ACTIVITY AND A PROCESS FOR THEIR PREPARATION

[76] Inventors: Iván Balkányi, Tündérlaki u. 6., H-1016 Budapest; Rudolf Szebeni, Béke u. 48., H-2131 Alsogöd; Ferenc Hadi, Dózsa György u. 13., H-2626 Nagymaros; Miklós Marsó, Árpád fejedelem u. 55/a., H-1036 Budapest; Éva Kéri, Kazinczy u.7.II.5., H-1075 Budapest; Béla Köszegi, Corvin krt. 52., H-1192 Budapest, all of Hungary

[21] Appl. No.: 742,466
[22] PCT Filed: Aug. 24, 1984
[86] PCT No.: PCT/HU84/00042
§ 371 Date: Apr. 19, 1985
§ 102(e) Date: Apr. 19, 1985
[87] PCT Pub. No.: WO85/00970
PCT Pub. Date: Mar. 14, 1985

[30] Foreign Application Priority Data

Aug. 26, 1983 [HU] Hungary ................................ 2993

[51] Int. Cl.$^4$ .............................................. A61K 31/44
[52] U.S. Cl. ..................................... 514/282; 514/910
[58] Field of Search ........................... 514/282, 910

[56] References Cited

U.S. PATENT DOCUMENTS

| 4,217,353 | 8/1980 | Smith | 514/282 |
| 4,267,182 | 5/1981 | Holaday et al. | 514/282 |
| 4,464,378 | 8/1984 | Hussain | 514/282 |

FOREIGN PATENT DOCUMENTS

| 876968 | 1/1979 | Belgium. | |
| EP0005636A1 | 11/1979 | European Pat. Off. . | |
| WO82/03768 | 11/1982 | PCT Int'l Appl. . | |
| 84/00889 | 3/1984 | PCT Int'l Appl. | 514/282 |

OTHER PUBLICATIONS

Holtzman-J. Pharm. & Exp. Therap. 189, 1, 51-60 (1974).
Chem. Abst. 97:85115s (1982)-Levine et al.
Chem. Abst. 99:19362j (1983)-Bodnar et al.
Chem. Abst. 100:17609m (1984)-Bellinger et al.
Chem. Abst. 100:61679h (1984)-Deviche et al.
Chem. Abst. 100:79769x (1984)-Dawson.
Chem. Abst. 101:103915k (1984)-Wager-Srdar et al.
Chem. Abst. 101:184401q (1984)-Thornhill et al.
Stephen G. Holtzman, Effects of Narcotic Antagonists on Fluid Intake in the Rat, Life Sciences, vol. 16, pp. 1465-1470, USA-Pergamon Press, Apr. 23, 1975.
Martindale, The Extra Pharmacopoeia, Twenty-Eighth Ed., Reynolds, pp. 1012-1013 and 1034, London, 1982.
The Pharmacological Basis of Therapeutics, Seventh Ed., Goodman & Gillman, pp. 524-527, New York.
Du Pont Pharmaceuticals Investigator Brochure, "Naltrexone Hydrochloride", Clinical Pharmacology, pp. 132-136.
J. Biol. Chem., vol. 7, pp. 1446-2449, (1979).
Eur. J. of Clin. Inv., 13, 22125, (1983).

Primary Examiner—Douglas W. Robinson
Attorney, Agent, or Firm—Karl F. Ross; Herbert Dubno

[57] ABSTRACT

This invention is concerned with pharmaceutical compositions having appetite reducing activity. The compositions contain (5α,6α)7,8-didehydro-4,5-epoxy-17-(2-propanyl)-morphinano-3,6-diol.

3 Claims, No Drawings

PHARMACEUTICAL COMPOSITIONS HAVING APPETITE REDUCING ACTIVITY AND A PROCESS FOR THEIR PREPARATION

CROSS REFERENCE TO RELATED APPLICATION

This application is a National Phase Application corresponding to PCT/H084/00042 filed Aug. 24, 1984 claiming priority under the International Convention of Hungarian National Application 2993/83 filed Aug. 26, 1985.

BACKGROUND OF THE INVENTION

One of the basic phenomena of life is that living creatures take food from their environment. Considering that for the living creatures both overfeeding and underfeeding are dangerous, simultaneously with the rise of the food intake also a system for controlling the food intake has been developed. Together with the development of life also this food intake control system became more and more developed and today it operates as a very complicated system "having several regulating circles". (A summary of some presumed and proved regulating mechanisms is given in The Lancet of Feb. 19, 1983 on pages 398 to 401.) One of these regulating mechanisms is based on the so called opioid endogenic peptides. This is supported by the observation that if a special opiate antagonist, naloxone [(5α)- 4,5-epoxy-3,14-dihydroxy-17-(2-propenyl)-morphinane-6-one] is administered to animals it is absorbed by the opiate receptors and thereby the food intake, the appetite and also the fluid intake of the animal is hindered. The observation that by the administration of endogenic (and exogenic) opiates the appetite of animals and humans can be increased shows that these compounds exert an influence on the nutrition (Am. J. Clin. Nutr., 35, 757–761, 1982 and Appetite, 2, 193–208, 1981).

While in the case of non-domesticated animals the regulating mechanisms function more or less properly and ensure the appropriate food intake of the animals, in the case of humans complications from overeating are a common problem.

This can be readily understood as in the case of humans, food intake is caused not only by the sensation of hunger and, often the degree of the food intake does not merely follow the demands of the organism, and the demands are often many time surpassed. It is true that by careful food intake obesity can be avoided but in many instances the decision in itself is not sufficient for changing the alimentary habits, therefore for carrying out the decision a medical support is necessary as well.

The best known slimming agents are desopimone (4-chloro-α,α-dimethyl-phenethylamine), gracidine (3-methyl-2-phenyl-morpholine) and teronac [5-(p-chlorophenyl)-2,5-dihydro-3H-imidazo[2,1-a]isoindole-5-ol].

Unfortunately the known slimming agents have several contraindications and side effects, so in the case of a great number of the patients requiring treatment these agents cannot be used.

The side effects of desopimone are the dilatation of the pupil, increase of the inner pressure of the eyes, vomiting, diarrhoea, abdominal pains, difficulty at the beginning of urination, headache, allergic exanthema, vertigo; and insomnia and nervosity as well as somnolence and sedative effect all appearing in about equal proportions.

Gracidine only with increased care can be administered in the case of obesity associated with heart diseases, cardiovascular troubles and hypertension. At the intake of gracidine and when it is administered continuously during the treatment the driving of vehicles, working above ground and on dangerous machines are prohibited. During its use and influence, respectively, also the consumption of alcoholic drinks is prohibited. According to new information the compositions containing gracidine are forbidden.

Teronac may cause mouth dryness, headache, nervosity, nausea, constipation, impairment of sleep, dizziness, tachycardia, reversible trouble of sexual functions, sweating, eczema, dilatation of the pupil, allergy. Also in case of glaucoma, heart-rhythm troubles, serious cardiac failure, renal insufficiencies, liver troubles, hypertension, cerebral disturbances, psychiatric diseases, gastric and intestinal ulcers, the drug is contraindicated.

On the basis of the aforesaid an appetite reducing composition is needed which does not show the side effects of the known compositions and which can be widely used without side effects.

As the active ingredient of a composition like this primarily those substances can be taken into consideration which exert their influence on the field of the central nervous system. Substances of this type are also the opiate antagonists mentioned above.

It is known that in obese people the food intake is reduced by naloxone (J. Clin. Endocrin, Metab., 55, 196–198, 1982). It has similar activity in Prader-Willi syndrome (The Lancet, 1980, 876–877), traumatic hypothalamic hyperphagia (Am. J. Clin. Nutr., 35, 757–761, 1982) and also in the case of healthy patients rendered hungry by 2-desoxy-glucose infusion.

The use of naloxone as active ingredient in appetite reducing compositions is unavoidably hindered by the fact that when administered per os it should be given in extremely high doses. But in the case of a widely used appetite reducing composition only the peroral administration can come into consideration.

The object of the present invention is to provide an appetite reducing composition which can be widely used without side effects and contraindications.

BRIEF DESCRIPTION OF THE INVENTION

The object of the present invention is attained by an appetite reducing composition containing as active ingredient nalorphine [(5α, 6α)-7,8-didehydro-4,5-epoxy-17-(2-propenyl)-morphinane-3,6-diol]. This composition can be administered perorally.

DETAILED DESCRIPTION OF THE INVENTION

According to the present invention nalorphine, preferably in the form of its salt prepared with a strong acid, such as a mineral acid, e.g. hydrochloric acid, hydrobromic acid, is formulated into pharmaceutical compositions with carriers, diluents, flavoring, aromatizing, coloring agents and other auxiliary materials normally used for the preparation of oral pharmaceutical compositions.

The pharmaceutical compositions of the present invention are prepared in the form of tablets, dragees, pilules, capsulated or chartulated powder compositions and various solutions, suspensions (such as liquid medicines, drops etc.).

According to a preferred embodiment of the invention one dosage unit or a low number of the dosage units (tablet, dragée, chartula, capsule, drop or spoonful amount) of the pharmaceutical composition contain the single dose. A dosage unit may contain of course more than more dose, in this case for example the tablets may be provided with scores in order to facilitate their division into fractional amounts.

The daily dose of the active ingredient is 15 to 30 mg. As the active ingredient, has been used as an antinarcotic, the actual dose can be easily determined by the physician on the basis of his skill, considering the individual reactivity and tolerance of the patient and the effect intended to be achieved. These doses may exceed the doses mentioned above or may be less than indicated. The daily dose may be divided into more single doses containing equal or different amounts of the active ingredient. Thus the constant active ingredient level can be easily ensured.

The invention relates to a process for reducing the appetite of humans or animals as well, wherein the effective dose of the composition of the present invention, e.g. the amount containing 15 to 30 mg of the active ingredient is administered to the person or to the animal to be treated.

It has been surprisingly found that during or after the treatment carried out with the pharmaceutical composition of the present invention, side effects (mouth dryness) attributable to the composition only very rarely and in a very mild form were observed. No side effect was observed which could have been connected to the narcotic effect of the opium derivatives. No dependence on the medicine has been risen, no habituation or withdrawal symptom was observed after the treatment.

The invention is illustrated by the following non limiting examples.

EXAMPLE 1

Tablet containing 5 mg of active ingredient
A powder mixture of the following composition is prepared:

| | |
|---|---|
| nalorphine hydrobromide | 5.0 g |
| colloidal silica | 1.0 g |
| magnesium stearate | 3.0 g |
| talc | 9.0 g |
| microcrystalline cellulose | 82.0 g |
| | 100.0 g |

From the powder mixture thus obtained after homogenisation tablets each weighing 100.00 mg are compressed under a pressure of 49–785 MPa (500–8000 kp/cm$^2$).

EXAMPLE 2

Tablet containing 10 mg of active ingredient
A powder mixture of the following composition is prepared:

| | |
|---|---|
| nalorphine hydrobromide | 10.0 g |
| colloidal silica | 1.0 g |
| magnesium stearate | 3.0 g |
| talc | 9.0 g |
| microcrystalline cellulose | 77.0 g |
| | 100.0 g |

From the powder mixture thus obtained after homogenisation tablets each weighing 100.00 mg are compressed under a pressure of 49–785 MPa (500–8000 kp/cm$^2$).

EXAMPLE 3

Tablet containing 20 mg of active ingredient
A powder mixture of the following composition is prepared:

| | |
|---|---|
| nalorphine hydrobromide | 20.0 g |
| talc | 3.0 g |
| magnesium stearate | 4.0 g |
| mannitol | 108.0 g |
| | 135.0 g |

From 15.0 g of starch and water a 3–5% granulating liquid is prepared. The powder mixture is granulated with the starch solution thus obtained. Granules having a diameter of about 1 mm are prepared. The granules are dried at a temperature of 50° C., then they are compressed under a pressure of 49–785 MPa (500–8000 kp/cm$^2$) into tablets each weighing 150.00 mg.

Clinical tests were carried out on obese voluntary patients with the tablets containing 5 mg of active ingredient prepared according to Example 1. The body weight was measured at the beginning and at the end of the test, the number of the tablets administered daily was also registered and at the end of the treatment the weight loss was calculated in terms of of kg/week. The following Table contains the data thus obtained together with the occasional side effects.

TABLE

| Number of patient | Body at admission | weight at discharge | Weight loss (kg/week) | Number of tablets per day | Side effect |
|---|---|---|---|---|---|
| 1. | 103.5 kg | 100.5 kg | 0.75 | 2 | mouth dryness |
| 2. | 92.0 kg | 84.5 kg | 1.07 | 1 | ø |
| 3. | 82.0 kg | 76.0 kg | 0.50 | 3 | ø |
| 4. | 80.0 kg | 78.0 kg | 0.66 | 3 | ø |
| 5. | 123.0 kg | 122.0 kg | 0.50 | 5 | ø |
| 6. | 87.0 kg | 85.0 kg | 1.0 | 3 | ø |
| 7. | 80.0 kg | 77.0 kg | 0.75 | 2 | ø |
| 8. | 84.0 kg | 79.0 kg | 0.83 | 2 | ø |
| 9. | 114.0 kg | 108.0 kg | 0.75 | 3 | obstipation |
| 10. | 78.0 kg | 72.0 kg | 1.0 | 4 | thirst |
| 11. | 100.0 kg | 87.0 kg | 2.1 | 3 | obstipation |
| 12. | 90.0 kg | 82.0 kg | 0.5 | 4 | obstipation |
| 13. | 114.0 kg | 98.0 kg | 0.7 | 3 | obstipation |
| 14. | 92.0 kg | 81.5 kg | 0.7 | 4 | obstipation |
| 15. | 124.0 kg | 108.0 kg | 0.8 | 3 | ø |
| 16. | 97.0 kg | 88.0 kg | 0.4 | 5 | ø |
| 17. | 75.0 kg | 68.0 kg | 0.7 | 6 | transitorial vertigo |
| 18. | 103.0 kg | 99.0 kg | 0.5 | 5 | ø |
| 19. | 83.0 kg | 75.0 kg | 1.0 | 4 | transitorial nausea |
| 20. | 96.0 kg | 77.0 kg | 1.1 | 3 | obstipation |
| 21. | 91.0 kg | 87.0 kg | 0.5 | 4 | ø |
| 22. | 86.0 kg | 75.0 kg | 1.5 | 5 | obstipation |
| 23. | 104.0 kg | 93.0 kg | 0.5 | 4 | ø |
| 24. | 78.0 kg | 72.0 kg | 0.7 | 4 | ø |
| 25. | 109.0 kg | 100.0 kg | 0.9 | 4 | obstipation |
| 26. | 119.0 kg | 106.0 kg | 1.0 | 4 | ø |
| 27. | 97.3 kg | 87.3 kg | 1.0 | 4 | ø |

TABLE-continued

| Number of patient | Body at admission | weight at discharge | Weight loss (kg/week) | Number of tablets per day | Side effect |
|---|---|---|---|---|---|
| 28. | 82.5 kg | 76.0 kg | 0.6 | 3 | ∅ |
| 29. | 126.2 kg | 115.0 kg | 1.3 | 3 | obstipation |
| 30. | 81.5 kg | 73.8 kg | 1.1 | 3 | ∅ |
| 31. | 83.0 kg | 75.0 kg | 0.8 | 3 | obstipation |
| 32. | 108.6 kg | 101.3 kg | 0.8 | 3 | transitorial vertigo sleepiness |
| 33. | 119.8 kg | 112.0 kg | 0.8 | 4 | obstipation |
| 34. | 115.0 kg | 110.5 kg | 0.9 | 4 | obstipation |
| 35. | 98.0 kg | 87.0 kg | 1.2 | 3 | ∅ |
| 36. | 97.0 kg | 90.0 kg | 1.1 | 3 | ∅ |
| 37. | 115.5 kg | 100.3 kg | 2.1 | 3 | ∅ |
| 38. | 125.0 kg | 102.5 kg | 1.3 | 3 | ∅ |
| 39. | 132.0 kg | 121.0 kg | 0.7 | 4 | ∅ |

We claim:

1. A method for exerting an anorexigenic effect in an animal subject which comprises orally administering to said subject an anorexigenic effective amount of nalorphine or a pharmaceutically acceptable salt thereof.

2. The method for exerting an anorexigenic effect defined in claim 1 wherein the animal subject is a person.

3. The method for exerting an anorexigenic effect defined in claim 1 wherein the therapeutically effective amount of the nalorphine or a pharamaceutically acceptable salt thereof is 15 to 30 mg/day.

* * * * *